United States Patent
Ogawa et al.

(10) Patent No.: US 9,632,577 B2
(45) Date of Patent: Apr. 25, 2017

(54) OPERATION SUPPORT DEVICE AND CONTROL METHOD THEREOF

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 261 days.

(21) Appl. No.: 14/169,742

(22) Filed: Jan. 31, 2014

(65) Prior Publication Data

US 2014/0148820 A1 May 29, 2014

Related U.S. Application Data

(63) Continuation of application No. PCT/JP2012/069927, filed on Jul. 30, 2012.

(Continued)

(30) Foreign Application Priority Data

Feb. 27, 2012 (JP) ................... 2012-040011

(51) Int. Cl.
*A61B 19/00* (2006.01)
*G06F 3/01* (2006.01)
(Continued)

(52) U.S. Cl.
CPC ............... *G06F 3/01* (2013.01); *A61B 17/29* (2013.01); *A61B 17/32002* (2013.01);
(Continued)

(58) Field of Classification Search
CPC ....... A61B 17/068; A61B 34/20; A61B 34/30; A61B 34/37; A61B 34/76; A61B 2034/2065

See application file for complete search history.

(56) References Cited

U.S. PATENT DOCUMENTS 3,139,990 A   7/1964  Jelatis et al.
3,923,166 A   12/1975 Fletcher et al.
(Continued)

FOREIGN PATENT DOCUMENTS

CN   101027010 A   8/2007
CN   101167658 A   4/2008
(Continued)

OTHER PUBLICATIONS

Japanese Office Action dated Jan. 19, 2016 from related Japanese Patent Application No. 2012-036226, together with an English language translation.

(Continued)

*Primary Examiner* — Julie A Szpira
(74) *Attorney, Agent, or Firm* — Scully, Scott, Murphy & Presser, P.C.

(57) ABSTRACT

An operation support device includes a manipulation input unit that outputs a manipulation command in accordance with an input from an operator, and a motion unit that causes a surgical instrument to move in accordance with the manipulation command. The manipulation input unit includes an object-to-be-detected that is gripped by the operator and a detection device that detects the object-to-be-detected. The object-to-be-detected includes a body part that has a first marker, which is detected by the detection device, disposed thereon, a manipulation part that is disposed in the body part and that is manipulated by the operator, and a second marker that is disposed in at least one of the body part and the manipulation part.

14 Claims, 9 Drawing Sheets

Related U.S. Application Data

(60) Provisional application No. 61/515,203, filed on Aug. 4, 2011.

(51) Int. Cl.

| | | |
|---|---|---|
| *A61B 17/29* | (2006.01) | |
| *A61B 17/32* | (2006.01) | |
| *A61B 18/14* | (2006.01) | |
| *B25J 9/16* | (2006.01) | |
| *B25J 13/02* | (2006.01) | |
| *A61B 34/30* | (2016.01) | |
| *A61B 46/10* | (2016.01) | |
| *A61B 34/37* | (2016.01) | |
| A61B 17/068 | (2006.01) | |
| A61B 17/00 | (2006.01) | |
| A61B 46/23 | (2016.01) | |
| A61B 34/20 | (2016.01) | |
| A61B 90/00 | (2016.01) | |
| A61B 34/00 | (2016.01) | |

(52) U.S. Cl.
CPC .......... *A61B 18/1402* (2013.01); *A61B 34/30* (2016.02); *A61B 34/37* (2016.02); *A61B 34/74* (2016.02); *A61B 34/76* (2016.02); *A61B 34/77* (2016.02); *A61B 46/10* (2016.02); *B25J 9/1689* (2013.01); *B25J 13/02* (2013.01); A61B 17/068 (2013.01); A61B 34/20 (2016.02); A61B 34/25 (2016.02); A61B 46/23 (2016.02); A61B 2017/00119 (2013.01); A61B 2017/00477 (2013.01); A61B 2017/00482 (2013.01); A61B 2034/2055 (2016.02); A61B 2034/2065 (2016.02); A61B 2090/067 (2016.02); A61B 2090/3937 (2016.02); Y10S 901/08 (2013.01); Y10S 901/09 (2013.01); Y10S 901/30 (2013.01); Y10T 29/49826 (2015.01); Y10T 74/18056 (2015.01)

(56) References Cited

U.S. PATENT DOCUMENTS

| | | |
|---|---|---|
| 4,672,281 A | 6/1987 | Yagusic et al. |
| 4,830,569 A | 5/1989 | Jannborg |
| 4,872,803 A | 10/1989 | Asakawa |
| 5,214,969 A | 6/1993 | Adkins et al. |
| 5,603,723 A | 2/1997 | Aranyi et al. |
| 5,632,432 A | 5/1997 | Schulze et al. |
| 5,649,956 A | 7/1997 | Jensen et al. |
| 5,656,903 A | 8/1997 | Shui et al. |
| 5,712,543 A | 1/1998 | Sjostrom |
| 5,760,530 A | 6/1998 | Kolesar |
| 5,762,458 A | 6/1998 | Wang et al. |
| 5,784,542 A | 7/1998 | Ohm et al. |
| 5,817,119 A | 10/1998 | Klieman et al. |
| 5,836,869 A | 11/1998 | Kudo et al. |
| 5,855,583 A | 1/1999 | Wang et al. |
| 5,871,493 A | 2/1999 | Sjostrom et al. |
| 5,876,325 A | 3/1999 | Mizuno et al. |
| 6,007,550 A | 12/1999 | Wang et al. |
| 6,039,748 A | 3/2000 | Savage et al. |
| 6,063,095 A | 5/2000 | Wang et al. |
| 6,082,797 A | 7/2000 | Antonette |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 | 3/2001 | Ramans |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Wang et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 * | 6/2014 | Sakai ............... G06F 3/017 382/115 |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 * | 3/2016 | Hager .............. B25J 9/1671 |
| 9,308,009 B2 | 4/2016 | Madan et al. |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033024 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |

(56) References Cited

U.S. PATENT DOCUMENTS

| | | |
|---|---|---|
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |
| 2012/0323364 A1* | 12/2012 | Birkenbach ............ G06F 3/014 700/257 |

FOREIGN PATENT DOCUMENTS

| | | | |
|---|---|---|---|
| CN | 101426412 A | 5/2009 | |
| DE | 10 2008 041 867 A1 | 3/2010 | |
| DE | WO 2011085815 A1 * | 7/2011 | ............ G06F 3/014 |
| EP | 0 677 278 A1 | 10/1995 | |
| EP | 1 728 475 A2 | 12/2006 | |
| EP | 2 092 875 A1 | 8/2009 | |
| EP | 2 298 220 A1 | 3/2011 | |
| EP | 2 332 484 A2 | 6/2011 | |
| JP | 63-029810 A | 2/1988 | |
| JP | 64-034688 A | 2/1989 | |
| JP | 01-271185 A | 10/1989 | |
| JP | 02-071980 A | 3/1990 | |
| JP | 02-292193 A | 12/1990 | |
| JP | 03-161289 A | 7/1991 | |
| JP | 05-096477 A | 4/1993 | |
| JP | 5-329784 A | 12/1993 | |
| JP | 07-001366 A | 1/1995 | |
| JP | 07-194609 A | 8/1995 | |
| JP | 07-241300 A | 9/1995 | |
| JP | 07-246578 A | 9/1995 | |
| JP | 07-096182 B2 | 10/1995 | |
| JP | 8-66883 A | 3/1996 | |
| JP | 08-215204 A | 8/1996 | |
| JP | 08-243080 A | 9/1996 | |
| JP | H10-502265 A | 3/1998 | |
| JP | 10-128538 A | 5/1998 | |
| JP | 11-300662 A | 11/1999 | |
| JP | 2000-312684 A | 11/2000 | |
| JP | 2001-087281 A | 4/2001 | |
| JP | 2001-113481 A | 4/2001 | |
| JP | 2001-277157 A | 10/2001 | |
| JP | 2001-309920 A | 11/2001 | |
| JP | 2002-014287 A | 1/2002 | |
| JP | 2002-059380 A | 2/2002 | |
| JP | 2002-102248 A | 4/2002 | |
| JP | 2002-272758 A | 9/2002 | |
| JP | 2002-537884 A | 11/2002 | |
| JP | 2003-024336 A | 1/2003 | |
| JP | 2003-053685 A | 2/2003 | |

(56) References Cited

FOREIGN PATENT DOCUMENTS

| | | |
|---|---|---|
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-104854 A | 5/2008 |
| JP | 2008-514357 A | 5/2008 |
| JP | 2008-173724 A | 7/2008 |
| JP | 2008-188109 A | 8/2008 |
| JP | 4129313 B2 | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226029 A | 10/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-091310 A | 5/2012 |
| WO | 96/00044 A1 | 1/1996 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | 00/51486 A1 | 9/2000 |
| WO | 00/60421 A2 | 10/2000 |
| WO | 03/049596 A2 | 6/2003 |
| WO | 2006/039092 A2 | 4/2006 |
| WO | 2006/111966 A2 | 10/2006 |
| WO | 2007/047782 A2 | 4/2007 |
| WO | 2007/075864 A1 | 7/2007 |
| WO | 2007/111955 A2 | 10/2007 |
| WO | 2007/126443 A2 | 11/2007 |
| WO | 2007/138674 A1 | 12/2007 |
| WO | 2008/038184 A2 | 4/2008 |
| WO | 2008/108289 A1 | 9/2008 |
| WO | 2009/034477 A2 | 3/2009 |
| WO | 2009/089614 A1 | 7/2009 |
| WO | 2010/006057 A1 | 1/2010 |
| WO | 2010/093152 A2 | 8/2010 |
| WO | 2010/109932 A1 | 9/2010 |
| WO | 2010/126127 A1 | 11/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | 2012/042949 A1 | 4/2012 |

OTHER PUBLICATIONS

Office Action dated Feb. 22, 2016 received in related U.S. Appl. No. 14/168,496.
Office Action dated Mar. 10, 2016 received in related U.S. Appl. No. 13/566,012.
Office Action dated Nov. 19, 2015 received in related U.S. Patent Application, namely U.S. Appl. No. 14/157,920.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Patent Application, namely U.S. Appl. No. 14/169,321.
Extended Supplementary European Search Report dated Mar. 27, 2015 from related European Application No. 12 82 0056.5.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.
Office Action dated May 9, 2016 received in related U.S. Appl. No. 14/170,856.
English Abstract of JP 01-234140 dated Sep. 19, 1989.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.

(56) References Cited

OTHER PUBLICATIONS

International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
U.S. Office Action dated Apr. 9, 2015 received in related U.S. Patent Application, namely U.S. Appl. No. 14/169,675.
U.S. Office Action dated May 8, 2015 received in related U.S. Patent Application, namely U.S. Appl. No. 14/157,920.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Office Action dated Sep. 16, 2015 received in related U.S. Patent Application, namely U.S. Appl. No. 13/566,012.
Office Action dated Oct. 19, 2015 received in related U.S. Patent Application, namely U.S. Appl. No. 14/168,525.
Office Action dated Oct. 22, 2015 received in related U.S. Patent Application, namely U.S. Appl. No. 14/151,987.
Office Action dated Mar. 24, 2016 received in related U.S. Appl. No. 13/566,047.
Japanese Office Action dated Jun. 14, 2016 in related Japanese Patent Application No. 2012-012104.
Japanese Office Action dated Jun. 28, 2016 in related Japanese Patent Application No. 2013-526973.
European Patent Office Communication dated May 23, 2016 in related European Application No. 12 819 877.7.
Japanese Office Action dated Jan. 4, 2017 in related Japanese Patent Application No. 2012-012104.
Office Action dated Feb. 28, 2017 received in related U.S. Appl. No. 14/168,496.

* cited by examiner

OPERATION SUPPORT DEVICE AND CONTROL METHOD THEREOF

This application is a continuation application based on a PCT Patent Application No. PCT/JP2012/069927, filed on Jul. 30, 2012, whose priority is claimed on Japanese Patent Application No. 2012-040011, filed on Feb. 27, 2012, and U.S. Provisional Patent Application No. 61/515,203, filed Aug. 4, 2011. The contents of all of the PCT Application, the Japanese Application, and the U.S. Provisional Patent Application are incorporated herein by reference.

TECHNICAL FIELD

The present invention relates to an operation support device that is remotely manipulated and a control method thereof.

BACKGROUND ART

Conventionally, a master-slave type operation support device having a master manipulator that is manipulated by an operator and a slave manipulator that moves based on a signal output from the master manipulator is known as an operation support device.

It is known that an operation support device is caused to work using a tracking device that detects the position and the orientation and the opening and closing state of an operator's hand (for example, see U.S. Patent Publication No. 2011/0118753).

The tracking device described in U.S. Patent Publication No. 2011/0118753 includes a glove with multiple markers attached thereto and a detector detecting the positions of the marker. Accordingly, when an operator wears the glove with the markers attached thereto and moves his/her hand, it is possible to cause the slave manipulator to work based on the position and the orientation and the opening and closing state of the hand.

SUMMARY OF INVENTION

According to a first aspect of the present invention, an operation support device includes a manipulation input unit that outputs a manipulation command in accordance with an input from an operator, and a motion unit that causes a surgical instrument to move in accordance with the manipulation command. The manipulation input unit includes an object-to-be-detected that is gripped by the operator and a detection device that detects the object-to-be-detected. The object-to-be-detected includes a body part that has a first marker, which is detected by the detection device, disposed thereon, a manipulation part that is disposed in the body part and that is manipulated by the operator, and a second marker that is disposed in at least one of the body part and the manipulation part. A state of the second marker changes in response to a manipulation on the manipulation part. The detection device calculates information which is capable of specifying a position and an orientation of the object-to-be-detected using at least the first marker and calculates information which is capable of specifying a manipulation input state to the manipulation part using at least the second marker. The manipulation input unit outputs a command as the manipulation command to the motion unit based on a result calculated by the detection device, for causing the surgical instrument to move, so as to control a movement of the surgical instrument in accordance with the position of the object-to-be-detected, the orientation of the object-to-be-detected, and the manipulation input state.

According to a second aspect of the invention, in the operation support device according to the first aspect of the present invention, the manipulation part may be movably connected to the body part, the second marker may be disposed in the manipulation part, and the detection device may calculate a position and an orientation of the body part using at least the first marker and calculates the manipulation input state to the manipulation part based on the position of the second marker.

According to a third aspect of the present invention, in the operation support device according to the second aspect of the present invention, the manipulation part may be capable of being opened and closed with respect to the body part.

According to a fourth aspect of the invention, in the operation support device according to any one of the first to third aspects of the present invention, a first position at which the first marker is located and a second position at which the second marker is located may be different from each other, the first marker may be different from the second marker in at least one item other than the first position and the second position, and the detection device may distinguish between the first marker and the second marker based on the item.

According to a fifth aspect of the present invention, in the operation support device according to any one of the first to third aspects of the present invention, a first position at which the first marker is located and a second position at which the second marker is located may be only different from each other, and the detection device may distinguish between the first marker and the second marker based on only a relative positional relationship between the first position of the first marker and the second position of the second marker on the manipulation input unit.

According to a sixth aspect of the present invention, in the operation support device according to the third aspect of the present invention, the detection device may calculate the position and the orientation of the body part, and the manipulation input state using both the first marker and second marker.

According to a seventh aspect of the invention, in the operation support device according to the fourth aspect of the present invention, an amount of state of the second marker may change depending on an amount of manipulation of the manipulation part.

According to an eighth aspect of the invention, a control method of an operation support device that controls the operation support device using an object-to-be-detected having a body part with a first marker attached thereto and a manipulation part with a second marker attached thereto may include detecting the first marker and the second marker of the object-to-be-detected; calculating a first information which is capable of specifying a position and an orientation of the object-to-be-detected using at least a detected first marker and calculating a second information which is capable of specifying a manipulation input state to the manipulation part using at least a detected second marker; and controlling movement of a surgical instrument disposed in the operation support device using the first information and the second information.

DESCRIPTION OF EMBODIMENTS

First Embodiment

Figure 1:
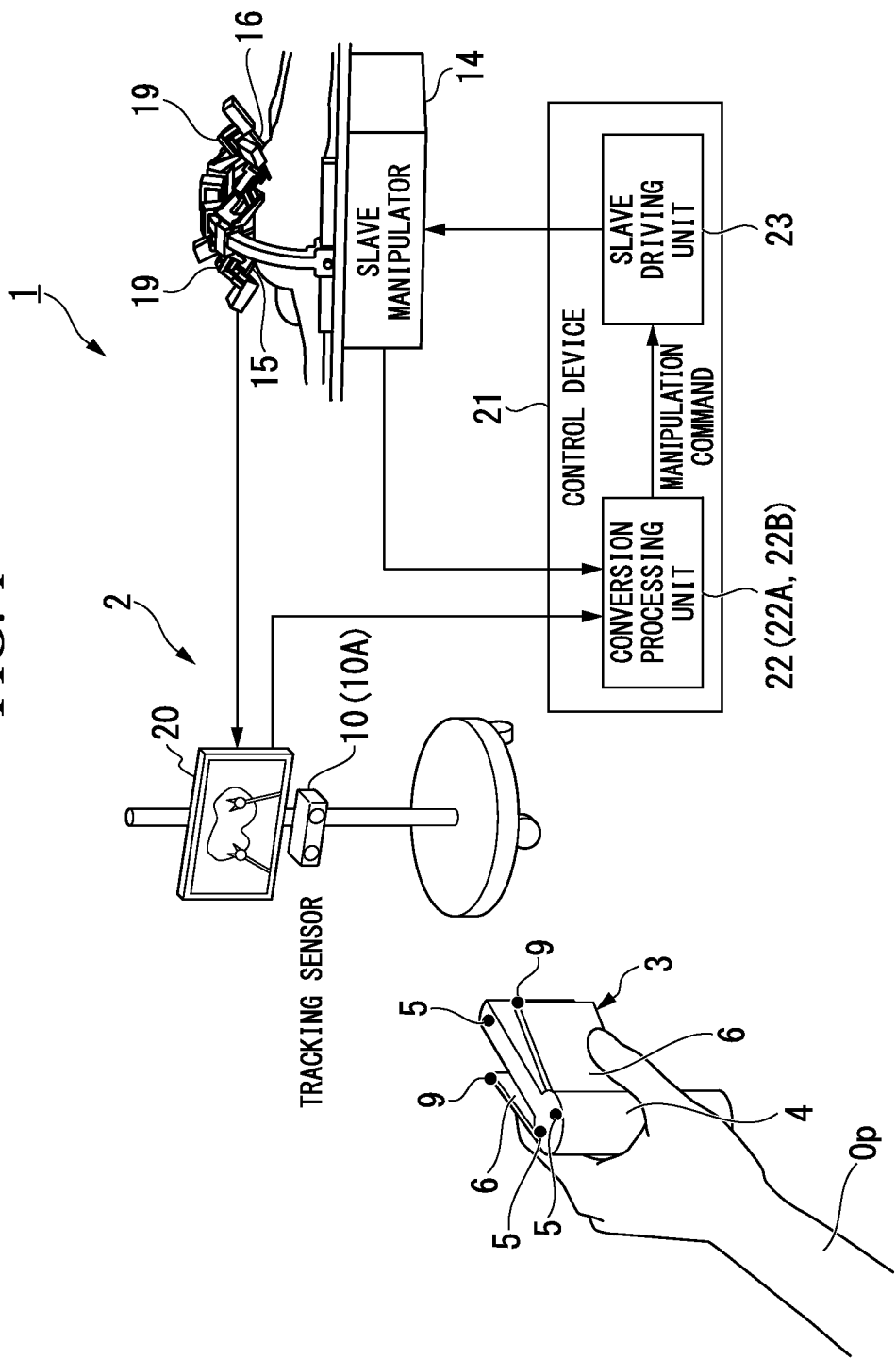
FIG. 1 is a diagram illustrating the entire configuration of an operation support device according to a first embodiment of the present invention.
Figure 2:
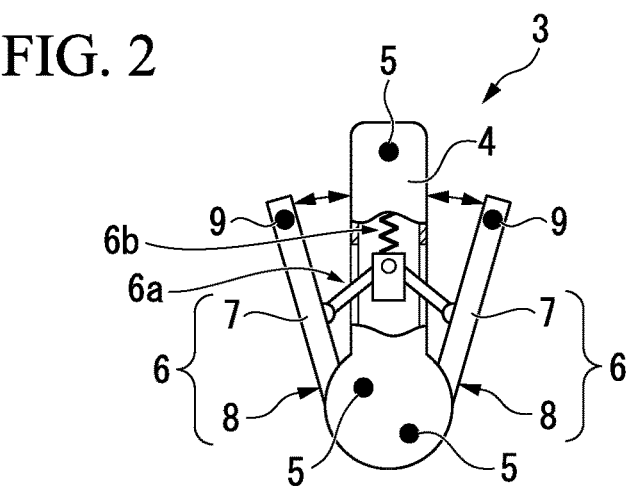
FIG. 2 is a plan view illustrating an object-to-be-detected in the operation support device according to the first embodiment of the present invention.
Figure 3:
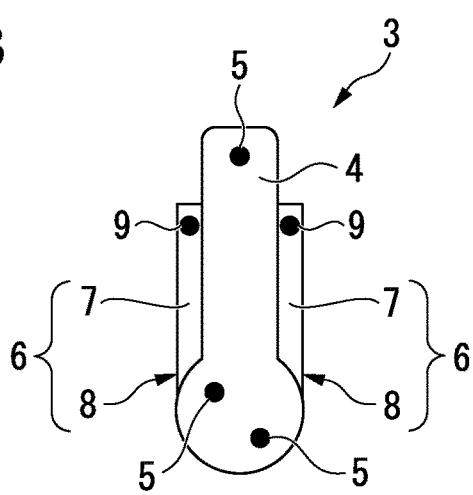
FIG. 3 is a plan view illustrating the object-to-be-detected according to the first embodiment of the present invention.
Figure 4:
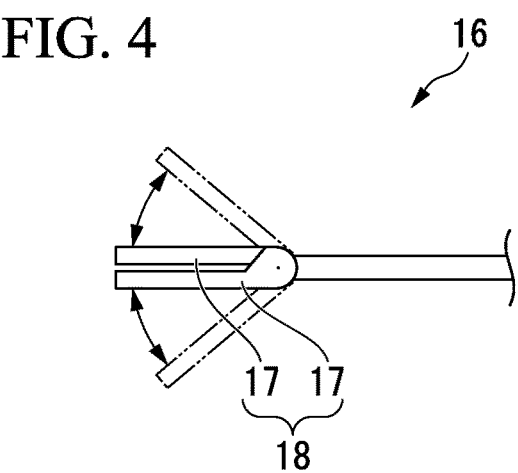
FIG. 4 is a schematic diagram illustrating an example of a surgical instrument provided to the operation support device according to the first embodiment of the present invention.

An operation support device 1 and a control method thereof according to a first embodiment of the present invention will be described below. FIG. 1 is a diagram illustrating the entire configuration of the operation support device according to the first embodiment. FIG. 2 is a plan view illustrating an object-to-be-detected in the operation support device according to the first embodiment of the present invention. FIG. 3 is a plan view illustrating the object-to-be-detected according to the first embodiment of the present invention. FIG. 4 is a schematic diagram illustrating an example of a surgical instrument provided to the operation support device according to the first embodiment of the present invention.

As shown in FIG. 1, the operation support device 1 includes a master manipulator (manipulation input unit) 2, a slave manipulator (motion unit) 14, a display device 20, and a control device 21.

The master manipulator 2 serves to cause the slave manipulator 14 to move in response to movement of an operator Op and includes an object-to-be-detected 3 that is gripped by the operator Op and the detection device 10 that detects the object-to-be-detected 3. In the first embodiment, the master manipulator 2 and a conversion processing unit 22 of the control device 21 configure a manipulation input unit that outputs a manipulation command for causing the salve manipulator 14 to move.

As shown in FIGS. 1 and 2, the object-to-be-detected 3 is provided to allow the operator Op gripping the object-to-be-detected 3 to perform a manipulation to the master manipulator 2. The object-to-be-detected 3 includes a body part 4 and a manipulation part 6 movably connected to the body part 4.

The body part 4 is a member having first markers 5 attached to the outer surface of the body part 4. The first markers 5 attached to the body part 4 are arranged at three positions separated from each other on the outer surface of the body part 4. The first markers 5 are disposed on the outer surface of the body part 4, for example, by printing.

The first markers 5 are positioned and arranged on the body part 4. Accordingly, positions and orientations of the first markers 5 correspond to a position and an orientation of the body part 4. The three first markers 5 are arranged so that the lengths of three sides of a triangle having the first markers 5 as vertexes are different from each other. As a result, it is possible to uniquely specify the orientation of the body part 4 based on the relative positional relationship of the first markers 5.

In the first embodiment, in order to allow one of cameras disposed in an imaging unit 11 to be described later to capture images of all the first markers 5, the first markers 5 are arranged in a planar portion or a very-gently-curved portion on the outer surface of the body part 4.

Three or more extra markers may be provided extra so as to cope with a case where a certain first marker 5 out of the three first markers 5 is shielded during manipulation. When the certain one first marker 5 out of the three first markers 5 is shielded, the position and the orientation are calculated by using one of the extra markers as the first maker 5.

Three or more first markers 5 may be arranged on a sheet that the sheet may be attached to the outer surface of the body part 4.

As shown in FIG. 1, the manipulation part 6 is provided to manipulate a surgical instrument 16 disposed in the slave manipulator 14 and is manipulated by the operator Op. In the first embodiment, the manipulation part 6 is provided to open and close a pair of forceps pieces 17 disposed in a treatment portion 18 of a gripping forceps which is the surgical instrument 16 (see FIG. 4). The manipulation part 6 includes a pair of rod-shaped portions 7 protruding from the outer surface of the body part 4, as shown in FIGS. 2 and 3. An end of each rod-shaped portion 7 is provided with a pivot portion 8 supporting the rod-shaped portion 7 to be rotatable relative to the body part 4. The second marker 9 of which the state varies depending on the manipulation on the manipulation part 6 is attached to the other end of each rod-shaped portion 7.

In the first embodiment, the second marker 9 moves along with the manipulation part 6 in response to the manipulation on the manipulation part 6. In the first embodiment, a second position at which the second marker 9 is located is different from a first position at which the first marker 5 is located, but the first marker 5 and the second marker 9 have the same configuration except for the locations.

The pair of rod-shaped portions 7 are arranged to face to each other with the body part 4 interposed therebetween. By causing the respective rod-shaped portions 7 to rotate about the corresponding pivot portions 8, the manipulation part 6 can perform an opening and closing motion corresponding to the motion of the pair of forceps pieces 17 disposed in the surgical instrument 16. For example, an opening and closing mechanism of the manipulation part 6 includes a link mechanism 6a and a biasing member 6b biasing the link mechanism 6a to open the rod-shaped portions 7.

Figure 5:
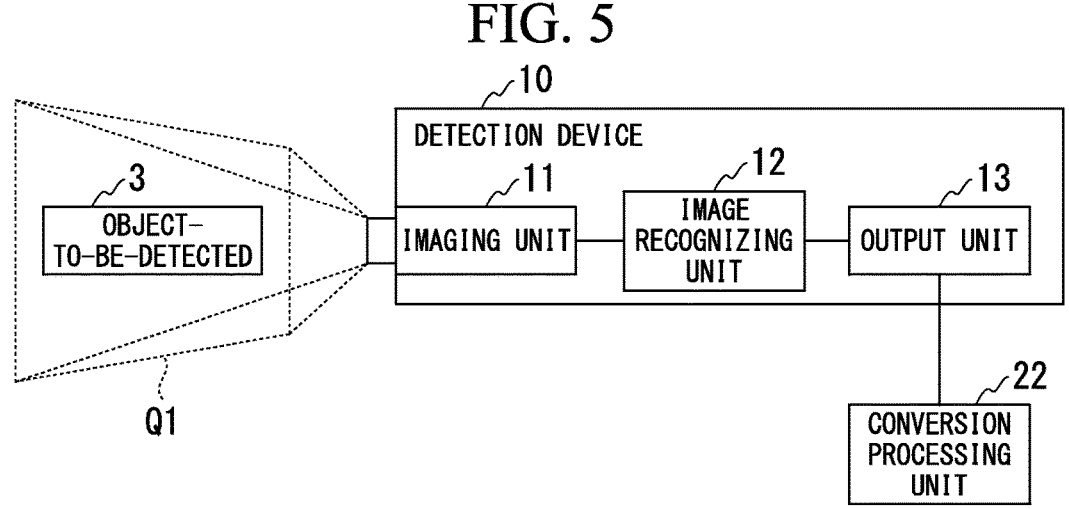
FIG. 5 is a schematic diagram illustrating the configuration of a detection device in the operation support device according to the first embodiment of the present invention.
Figure 6:
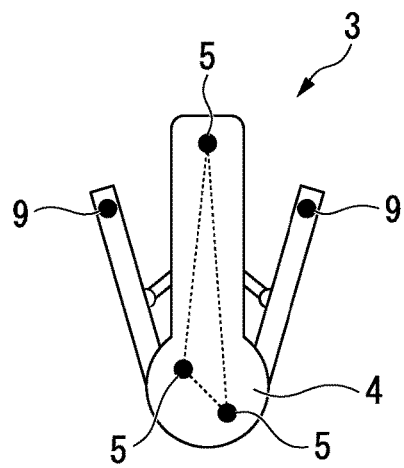
FIG. 6 is a diagram illustrating a method of detecting the object-to-be-detected in the operation support device according to the first embodiment of the present invention.
Figure 7:
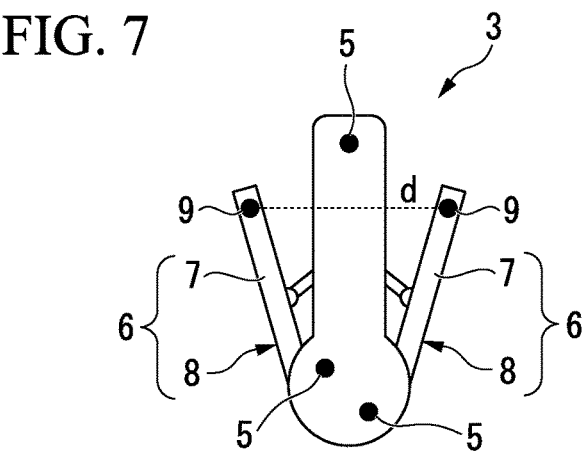
FIG. 7 is a diagram illustrating the method of detecting the object-to-be-detected in the operation support device according to the first embodiment of the present invention.

FIG. 5 is a schematic diagram illustrating the configuration of the detection device in the operation support device according to the first embodiment of the present invention. FIGS. 6 and 7 are diagrams illustrating a method of detecting the object-to-be-detected in the operation support device according to the first embodiment of the present invention.

As shown in FIG. 5, the detection device 10 includes an imaging unit 11, an image recognizing unit 12, and an output unit 13.

The detection device 10 calculates information which is capable of specifying the position and the orientation of the object-to-be-detected 3 using at least the first markers 5 and calculates information which is capable of specifying the manipulation input state to the manipulation part 6 using at least the second markers 9.

The master manipulator 2 controls the movement of the surgical instrument 16 based on the position and the orientation of the object-to-be-detected 3 and the manipulation input state by outputting a command of moving the surgical instrument 16 as a manipulation command to the slave manipulator 14 based on the calculation result of the detection device 10.

The imaging unit 11 is a device imaging the object-to-be-detected 3 when the object-to-be-detected 3 is used by a user. An imaging field of view of the imaging unit 11 is set to be capable of imaging the overall space (hereinafter, referred to as a "working space Q1") in which the object-to-be-detected 3 is moved by the user when using the operation support device 1. The imaging unit 11 includes at least a first camera capturing an image of the working space Q1 from a predetermined direction and a second camera capturing an image from a direction other than the predetermined direction. Accordingly, the imaging unit 11 is capable of capturing at least two images of the object-to-be-detected 3 located in the working space Q1 from different angles simultaneously. The imaging unit 11 may include three or more cameras. The imaging unit 11 may include a preliminary camera as a redundancy configuration to cope with a case where the operator Op or another obstacle is interposed between the object-to-be-detected 3 and the cameras. The imaging unit 11 outputs the captured image to the image recognizing unit 12.

The image recognizing unit 12 separately recognizes the first markers 5 and the second markers 9 through an image recognizing process on the captured image. In the first embodiment, the first positions of the first markers 5 and the second positions of the second markers 9 in the master manipulator 2 are different from each other, and the image recognizing unit 12 distinguishes the first markers 5 from the second markers 9 only based on the relative positional relationship between the first markers 5 and the second markers 9 on the master manipulator 2. For example, by storing patterns of the relative positional relationship between the first markers 5 and the second markers 9 in the image recognizing unit 12 and comparing the image input from the imaging unit 11 with the patterns stored in the image recognizing unit 12, the coordinates of the first markers 5 and the second markers 9 in the working space Q1 are acquired. In the first embodiment, since the positional relationship of the first markers 5 in the body part 4 is fixed, a triangle having the first markers 5 as vertexes can be first detected (see FIG. 6). Also, markers located outside the triangle can be detected as the second markers 9. In addition, known means can be appropriately employed as the image recognizing process.

The output unit 13 outputs the coordinates acquired by the image recognizing unit 12 as coordinate information to the conversion processing unit 22 of the control device 21. In the first embodiment, the coordinate information output from the output unit 13 includes an information (a first information) for allowing the conversion processing unit 22 to specify the position and the orientation of the object-to-be-detected 3 and an information (a second information) for allowing the conversion processing unit 22 to specify the manipulation input state to the manipulation part 6. The coordinate information is output from the output unit 13 at a predetermined transmission time regardless of the fact that the object-to-be-detected 3 moves in the working space Q1.

As shown in FIG. 1, the slave manipulator 14 includes slave arms 19 being provided with an endoscope device 15 and a surgical instrument 16 (hereinafter, also collectively referred to as "a surgical instrument and the like") and actuators (not shown). The actuators (not shown) are disposed to cause the slave arms 19 and the surgical instruments operating. The actuators disposed in the slave manipulator 14 operate in accordance with a drive signal output from the control device 21.

As shown in FIG. 1, the endoscope device 15 disposed in the slave manipulator 14 acquires an image of a treatment target or the surgical instrument 16, and outputs the acquired image to the display device 20.

The surgical instrument 16 is provided to treat the treatment target within the field of view of the endoscope device 15. Types of the surgical instrument 16 are not particularly limited, and known surgical instruments can be appropriately employed depending on the treatment details. The surgical instrument 16 is not limited to surgical instruments which can attached to the slave manipulator 14, but may be a treatment tool cooperating with the slave manipulator 14.

In the first embodiment, a gripping forceps including a pair of forceps pieces 17 which is capable of being opened and closed is described as an example of the surgical instrument 16 (see FIG. 4). In the gripping forceps, the forceps pieces 17 are connected to each other via a predetermined rotational shaft and the pair of forceps pieces 17 configures a treatment portion 18. The position and the orientation of the treatment portion 18 are detected by the position and orientation detecting device disposed in the gripping forceps or the slave arm 19. The position and the orientation of the treatment portion 18 detected by the position and orientation detecting device are output to the control device 21 or are referred to by the control device 21.

An example of the position and orientation detecting device is an encoder disposed in each joint shaft of the slave arm 19. The position and the orientation of the treatment portion 18 can be calculated by kinematically analyzing such joint displacements.

As shown in FIG. 1, the display device 20 is mounted on the same base as the detection device 10 of the master manipulator 2. The display device 20 is disposed in front of the operator Op. The display device 20 includes a display panel displaying an image acquired by the endoscope device 15. The display panel can appropriately employ a liquid crystal panel or an organic EL panel. The display panel may be a panel displaying a stereoscopic image. The display panel displaying a stereoscopic image may employ a configuration in which a right-eye image and a left-eye image can be separated by the use of a dedicated glasses or a configuration in which an image can be stereoscopically viewed with a naked eye.

The control device 21 includes a conversion processing unit 22 connected to the detection device 10 and a slave driving unit 23. The slave driving unit 23 is connected to the conversion processing unit 22 while being connected to the each of the actuators of the slave manipulator 14.

The conversion processing unit 22 acquires tracking information of the slave manipulator 14 indicating the positions and orientations of the surgical instrument 16 and the slave arms 19 and the state of the treatment portion 18 disposed in the surgical instrument 16 by using the position and orientation detecting device disposed in the slave manipulator 14. The tracking information of the slave manipulator 14 is stored in the conversion processing unit 22 as the positions and orientations of the surgical instrument 16 and the slave arms 19 and the position and the orientation of the treatment portion 18 in a predetermined three-dimensional space defined, for example, by an orthogonal coordinate system.

The coordinate information of the object-to-be-detected 3 output from the detection device 10 is input to the conversion processing unit 22. The coordinate information of the object-to-be-detected 3 is input to the conversion processing unit 22 at the predetermined transmission time and is acquired to the conversion processing unit 22 as tracking information of the object-to-be-detected 3 in the conversion processing unit 22.

The conversion processing unit 22 has a coordinate system converting function of matching the coordinate system of the tracking information of the object-to-be-detected 3 and the coordinate system of the tracking information of the slave manipulator 14 with each other. The conversion processing unit 22 has a scale converting function of matching the scales in the tracking information of the object-to-be-detected 3 and the scales in the tracking information of the slave manipulator 14 with each other. Through the use of the coordinate converting function and the scale converting function, the movement of the operator Op moving the object-to-be-detected 3 while watching the display device 20 can be appropriately converted into the movement of the slave manipulator 14. The conversion processing unit 22 also stores correspondence between the distances between the second markers 9 and the distance between the distal ends of the forceps pieces 17.

The conversion processing unit 22 outputs a manipulation command for operating the slave manipulator 14 to the slave driving unit 23. The manipulation command output from the conversion processing unit 22 includes, for example, a signal for specifying an actuator to be moved out of multiple actuators disposed in the slave manipulator 14 and a signal for specifying the amount of movement of the actuator.

The slave driving unit 23 drives the actuators of the slave manipulator 14 in accordance with the manipulation command from the conversion processing unit 22.

The control method and the operation of the operation support device 1 will be described below.

When using the operation support device 1, the operator Op grips the object-to-be-detected 3 and hooks fingers on the manipulation part 6 (see FIG. 1). When the operator Op moves the body part 4, the first markers 5 disposed in the body part 4 move along with the body part 4 (see FIGS. 2 and 3). The first markers 5 are imaged by the imaging unit 11 disposed in the detection device 10. The second markers 9 disposed in the manipulation part 6 move along with the manipulation part 6. The second markers 9 are imaged by the imaging unit 11 disposed in the detection device 10.

In the first embodiment, the first markers 5 and the second markers 9 are distinguished based on the arrangement patterns of the first markers 5 and the second markers 9 stored in the detection device 10 in advance. The detection device 10 detects the positions and orientations of the first markers 5, and the positions and orientations of the second markers 9 in a three-dimensional space (the working space) based on the orthogonal coordinate system having a front-rear axis, an up-down axis, and a right-left axis as coordinate axes in the orientation in which the operator faces the display device 20 and watches the display device 20.

Here, the orientations and positions of the first markers 5 correspond to the orientation and position of the body part 4 and the orientations and positions of the second markers 9 correspond to the orientation and position of the manipulation part 6. The detection device 10 outputs the coordinate information of the first markers 5 and the second markers 9 in the three-dimensional space defined in the detection device 10 to the conversion processing unit 22.

The conversion processing unit 22 compares the tracking information of the slave manipulator 14 acquired from the slave manipulator 14 with the coordinate information (the tracking information of the object-to-be-detected 3) output from the detection device 10 and controls the position and the orientation of the treatment portion 18, and the opening and closing of the forceps pieces 17 disposed in the treatment portion 18.

First, the control of the position and the orientation of the treatment portion 18 will be described.

The conversion processing unit 22 recognizes the position and the orientation of the body part 4 in the working space based on the coordinate information of the three first markers 5. When the relationship between the position and the orientation of the body part 4 recognized by the conversion processing unit 22, and the tracking information of the slave manipulator 14 is different from predetermined correspondence, the conversion processing unit 22 actives the slave driving unit 23 to move the slave arms 19 and the surgical instrument 16 so as to satisfy the predetermined correspondence. The conversion processing unit 22 performs the coordinate conversion and the scale conversion for matching the coordinate system of the working space with the coordinate system of the slave manipulator 14, creates a manipulation command using the converted information, and outputs the created manipulation command to the slave driving unit 23.

The control of the opening and closing of the forceps pieces 17 will be described below.

The conversion processing unit 22 calculates a distance d between each of the second markers 9 when it is measured along a virtual plane parallel to a virtual plane including all the three first markers 5 (see FIG. 7). In the first embodiment, the coordinates of the second markers 9 are calculated by the detection device 10, and the conversion processing unit 22 calculates the distance between the second markers 9 using the coordinates. When the relationship between the distance of each of the second markers 9 input to the conversion processing unit 22 and the distance between the distal ends of the forceps pieces 17 in the tracking information of the slave manipulator 14 is different from predetermined correspondence, the conversion processing unit 22 activates the slave driving unit 23 to change the opening degree of the forceps pieces 17 so as to satisfy the predetermined correspondence. Accordingly, the movement of the manipulation part 6 relative to the body part 4 is delivered as the opening and closing movement of the forceps pieces 17 of the slave manipulator 14.

In this way, the conversion processing unit 22 compares the tracking information of the slave manipulator 14 with the tracking information of the object-to-be-detected 3. Also, the conversion processing unit 22 outputs a manipulation command so as to match the tracking information of the slave manipulator 14 with the tracking information of the object-to-be-detected 3 when both tracking information pieces are different from each other. In accordance with the manipulation command output from the conversion processing unit 22, the slave driving unit 23 moves the slave arms 19 and the surgical instrument 16 so as to correspond to the position and the orientation of the object-to-be-detected 3 and the manipulation input state to the manipulation part 6.

As a result, the slave manipulator 14 moves to follow the movement of the object-to-be-detected 3.

As described above, the operation support device 1 according to the first embodiment detects the position and the orientation of the object-to-be-detected 3 through the use of the first markers 5 which are disposed in the body part 4 of the object-to-be-detected 3 and of which the predetermined positional relationship does not vary. The operation support device 1 according to the first embodiment detects the manipulation input state to the manipulation part 6 through the use of the second markers 9 which are disposed in the manipulation part 6 of the object-to-be-detected 3 and of which the predetermined positional relationship varies. Accordingly, since the first markers 5 and the second markers 9 can be separately detected as different markers, it is possible to accurately remotely input a manipulation with a simple configuration.

Since all the first markers 5 used to detect the position and the orientation of the object-to-be-detected 3 are positioned relative to the body part 4, it is easy to detect the position and the orientation thereof. Further, since the second markers 9 is capable of being distinguished based on the first markers 5 of which the positional relationship relative to the body part 4 is known, the configuration other than the positions at which the markers are located such as the first positions of the first markers 5 and the second positions of the second markers 9 may be the same as each other and it is thus to simplify the configuration.

Since the marker used to detect the position and the orientation and the marker used to detect the manipulation input state are separately disposed, it is possible to reduce an erroneous detection.

Modified Example 1-1

Figure 8:
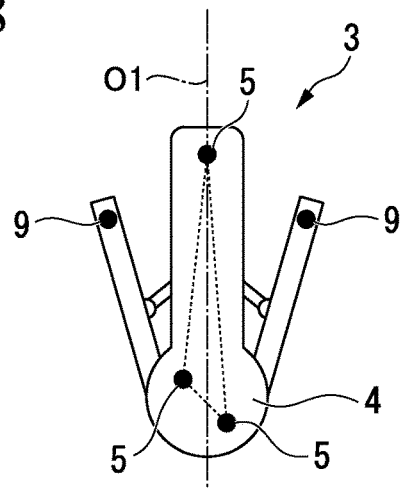
FIG. 8 is a diagram illustrating the method of detecting the object-to-be-detected in the operation support device according to the first embodiment of the present invention.
Figure 9:
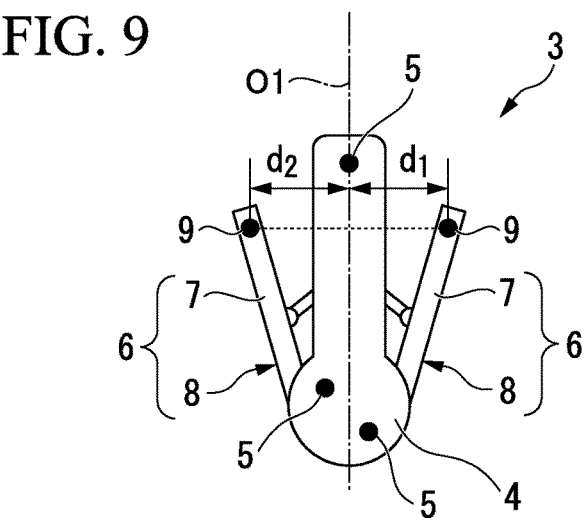
FIG. 9 is a diagram illustrating the method of detecting the object-to-be-detected in the operation support device according to the first embodiment of the present invention.

A modified example of the first embodiment will be described below. FIGS. 8 and 9 are diagrams illustrating a method of detecting an object-to-be-detected in the operation support device.

The modified example 1-1 is different from the first embodiment, in that the method of calculating the distance between the second markers 9 in the conversion processing unit 22.

The conversion processing unit 22 defines the central axis O1 of the body part 4 from the orientation detection result of the body part 4 using the first markers 5 (see FIG. 8). Subsequently, the distances d1 and d2 from the central axis O1 to the second markers 9 are individually calculated for the second markers 9 (see FIG. 9). Accordingly, in the modified example, the conversion processing unit 22 can calculate the manipulation input state to the manipulation part 6 in accordance with the variation in position of the second markers 9 relative to the body part 4.

In the modified example 1-1, even when one of the second markers 9 disposed in the manipulation part 6 is not imaged by the imaging unit 11 but the other is imaged by the imaging unit 11, the same detection result as in the above-mentioned embodiment is capable of being acquired.

Modified Example 1-2

Another modified example 1-2 of the first embodiment will be described below.

In the first embodiment, it has been stated that the first positions at which the first markers 5 are located are different from the second positions at which the second markers 9 are located. In the modified example 1-2, the first markers 5 are different from the second markers 9 in at least one item other than the first positions and the second positions.

For example, the first markers 5 and the second markers 9 have different colors. The imaging unit 11 can separately acquire at least the color of the first markers 5 and the color of the second markers 9. The detection device 10 separately acquires the coordinates of the first markers 5 and the coordinates of the second markers 9 and outputs the acquired coordinates to the conversion processing unit 22.

According to the configuration of the modified example 1-2, since the first markers 5 and the second markers 9 is capable of being distinguished from each other based on the colors, the conversion processing unit 22 does not need to perform the calculation of distinguishing the first markers 5 and the second markers 9 from the relative positional relationship of the first markers 5 and the second markers 9 and thus the calculation load is reduced. When a first marker 5 and a second marker 9 come close to each other, it is possible to reduce the possibility of erroneously recognizing the two markers.

Although it has been stated in the modified example 1-2 that the first markers 5 and the second markers 9 are distinguished based on the colors, the same advantages can be achieved by setting size, shape, figure, or light reflectance to be different in addition to the color.

The first markers 5 and the second markers 9 may be constructed by light sources 27 having different emission period or light intensities.

In this way, it is possible to distinguish the first markers 5 and the second markers 9 based on the difference (the item other than the first position and the second position) between the first markers 5 and the second markers 9.

Modified Example 1-3

Figure 10:
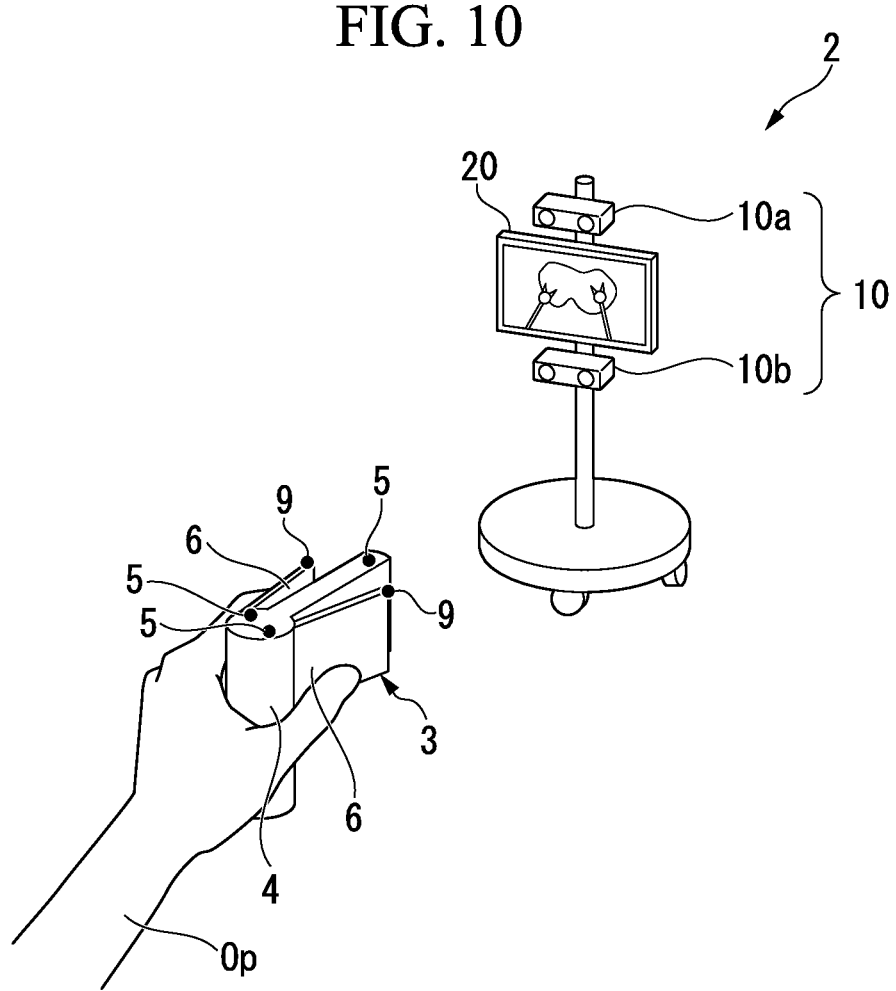
FIG. 10 is a schematic diagram illustrating a partial configuration of a modified example of the operation support device according to the first embodiment of the present invention.

Furthermore, another modified example 1-3 of the first embodiment will be described below. FIG. 10 is a diagram schematically illustrating a partial configuration of an operation support device according to the modified example 1-3.

In the modified example 1-3, as described in the modified example 1-2, the first markers 5 and the second markers 9 different from each other in color, size, shape, figure, light reflectance, emission period, or light intensity are provided. As shown in FIG. 10, the detection device 10 includes a first detection unit 10*a* detecting the first markers 5 and a second detection unit 10*b* detecting the second markers 9.

In the modified example 1-3, since a detection system for detecting the position and the orientation of the body part 4 and a detection system for detecting the manipulation state of the manipulation part 6 are independent of each other, it is possible to easily detect the manipulation on the manipulation part 6 and to enhance the detection accuracy.

Regarding the combination of the markers and the detection units in the modified example, an appropriate combination can be employed. Examples of the detection device including two types of cameras include a detection device including an infrared sensor and a color-distinguishable camera as the detection units, a detection device including cameras having different recognizable wavelengths as the detection units, a detection device including a wide-angle camera and a zoom camera as the detection units, and a detection device including cameras capturing an image with a delay of an imaging period so as to correspond to the emission periods of the first markers 5 and the second markers 9 as the detection units.

A detection device including two types of sensor systems may be used instead of the detection device including two types of cameras. Examples thereof include the following detection devices. A detection device including an optical sensor, which detects a reflective marker as the first marker 5, as a detection unit and a magnetic sensor, which detects a magnetic coil as the second marker 9, as a detection unit may be employed. A detection device including an ultrasonic sensor, which detects an ultrasonic wave generator as the second marker 9, as a detection unit may be employed. A detection device including a temperature sensor, which detects a heat source as the second marker 9, as a detection unit may be employed.

Instead of the detection device including two types of sensor systems, a detection device including one type of sensor system may be used. For example, a detection device including a single signal detecting unit detecting signal generators having different frequencies as the first marker 5 and the second marker 9 may be used. Examples of the signal include light frequency, electric wave frequency, and ultrasonic wave frequency.

Second Embodiment

An operation support device 1 according to a second embodiment of the present invention will be described below. In the second embodiment described below, the same elements as in the first embodiment are referenced by the same reference numerals and description thereof will not be repeated.

Figure 11:
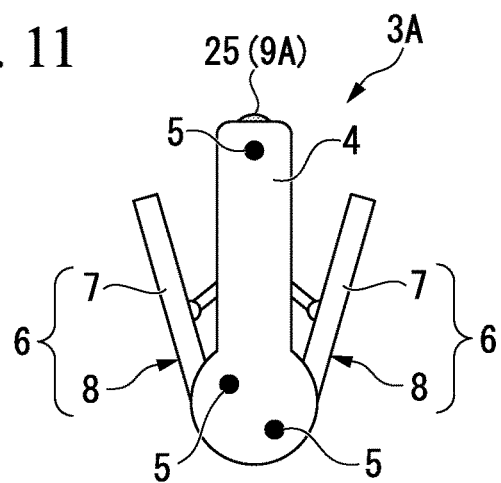
FIG. 11 is a plan view illustrating an object-to-be-detected provided to a operation support device according to a second embodiment of the present invention.
Figure 12:
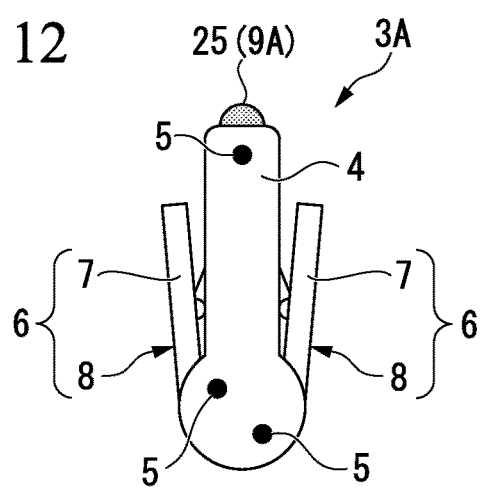
FIG. 12 is a plan view illustrating the object-to-be-detected according to the second embodiment of the present invention.
Figure 13:
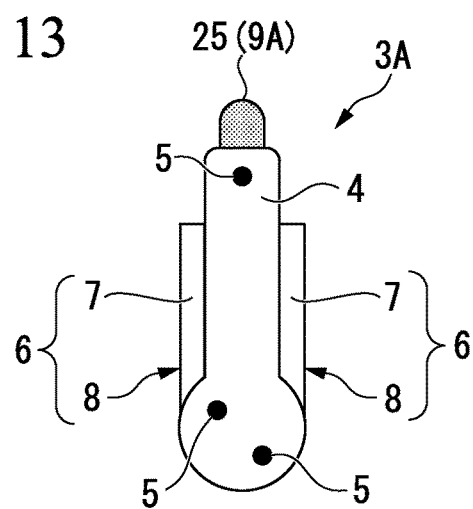
FIG. 13 is a plan view illustrating the object-to-be-detected according to the second embodiment of the present invention.

FIGS. 11 to 13 are plan views illustrating an object-to-be-detected disposed in the operation support device according to the second embodiment of the present invention.

As shown in FIGS. 1 and 11, the operation support device 1 according to the second embodiment is different from the operation support device according to the first embodiment, in that an object-to-be-detected 3A and a detection device 10A are provided instead of the object-to-be-detected 3 and the detection device 10 disposed in the master manipulator 2 and a conversion processing unit 22A is provided instead of the conversion processing unit 22 disposed in the control device 21.

The object-to-be-detected 3A includes a second marker 9A instead of the second markers 9.

As shown in FIGS. 11 to 13, the second marker 9A includes a linearly-moving rod 25 protruding and retreating with respect to the body part 4 with the rotational movement of the manipulation part 6. The linearly-moving rod 25 is connected to the rod-shaped portions 7 of the manipulation part 6 via a conversion mechanism such as a link converting the rotational movement about the pivot portion 8 into linear movement. In the second embodiment, when a pair of rod-shaped portions 7 is made to rotate about the pivot portions 8 to close the manipulation part 6, the linearly-moving rod 25 protrudes from the body part 4. When the pair of rod-shaped portions 7 is made to rotate about the pivot portions 8 to open the manipulation part 6, the linearly-moving rod 25 retreats into the body part 4. Accordingly, the protruding length of the linearly-moving rod 25 from the body part 4 is changed to correspond to the opening degree of the manipulation part 6.

The detection device 10A detects the first markers 5 similarly to the first embodiment.

The detection device 10A detects the second marker 9A instead of detecting the second markers 9 described in the first embodiment. The second marker 9A is detected by detecting the magnitude of the surface area of the portion of the linearly-moving rod 25 protruding from the body part 4. At this time, since the surface area of the linearly-moving rod 25 in an image varies depending on the distance between the object-to-be-detected 3 and the camera of the imaging unit 11, the surface area of the linearly-moving rod 25 is corrected from the magnitude in the image into the actual magnitude using the position information of the object-to-be-detected 3 in the working space Q1. The detection device 10A outputs the coordinate information on the body part 4 calculated using the first markers 5 and the surface area of the linearly-moving rod 25 calculated using the second marker 9A to the conversion processing unit 22A.

The conversion processing unit 22A controls the opening degree of the pair of forceps pieces 17 using the surface area of the linearly-moving rod 25 calculated by the detection device 10A. For example, when the linearly-moving rod 25 fully retreats into the body part 4, the area of the linearly-moving rod 25 protruding from the body part 4 is zero, which is made to correspond to a state where the pair of forceps pieces 17 is fully opened. The case where the area of the linearly-moving rod 25 protruding from the body part 4 is greater than a predetermined area is made to correspond to a state where the pair of forceps pieces 17 is fully closed. For example, the predetermined area can be set to an area of the linearly-moving rod 25 protruding from the body part 4 when the manipulation part 6 is fully closed.

In the second embodiment, the conversion processing unit 22A outputs a manipulation command for controlling the opening degree of the pair of forceps pieces 17 to the slave driving unit 23 based on the variation in surface area of the linearly-moving rod 25 disposed in the second marker 9A. With the configuration of the second embodiment, the slave manipulator 14 is capable of being made to interlock with the manipulation on the object-to-be-detected 3, similarly to the first embodiment.

Instead of using the method of controlling the variation in surface area of the linearly-moving rod 25, the opening degree of the forceps pieces 17 may be controlled based on the variation in distance between the distal end and the proximal end of the linearly-moving rod 25.

Modified Example 2-1

Figure 14:
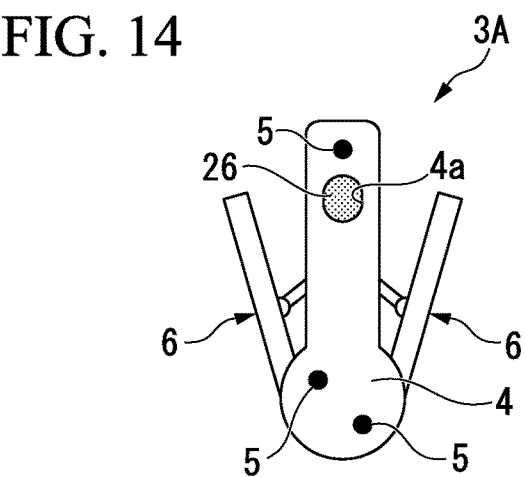
FIG. 14 is a plan view illustrating an object-to-be-detected according to a modified example of the second embodiment of the present invention.
Figure 15:
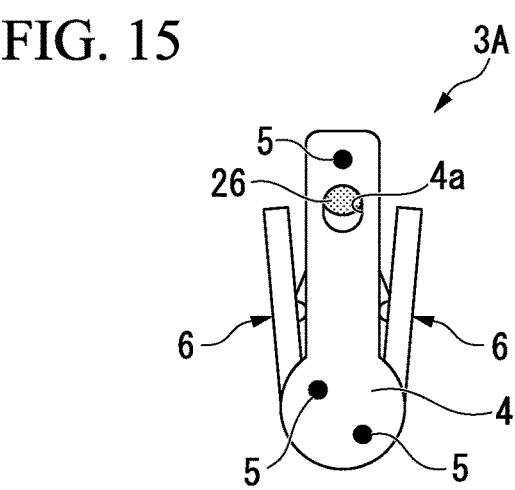
FIG. 15 is a plan view illustrating the object-to-be-detected according to the modified example of the second embodiment of the present invention.
Figure 16:
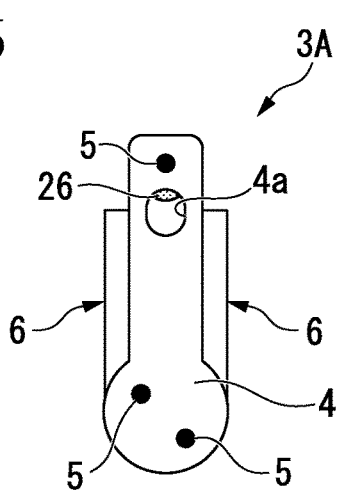
FIG. 16 is a plan view illustrating the object-to-be-detected according to the modified example of the second embodiment of the present invention.

A modified example 2-1 of the second embodiment will be described below. FIGS. 14 to 16 are plan views illustrating an object-to-be-detected in the modified example 2-1.

As shown in FIGS. 14 to 16, the modified example 2-1 is different from the second embodiment, in that a window 4a is formed in the body part 4 and a linearly-moving member 26 is disposed inside the body part 4 instead of the linearly-moving rod 25 protruding and retreating with respect to the body part 4.

By causing the linearly-moving member 26 to move in the window 4a, the exposed area of the linearly-moving member 26 varies.

In the modified example 2-1, it is possible to instruct the opening degree of the pair of forceps pieces 17 using the exposed area of the linearly-moving member 26 with respect to the opening area of the window 4a.

Modified Example 2-2

Figure 17:
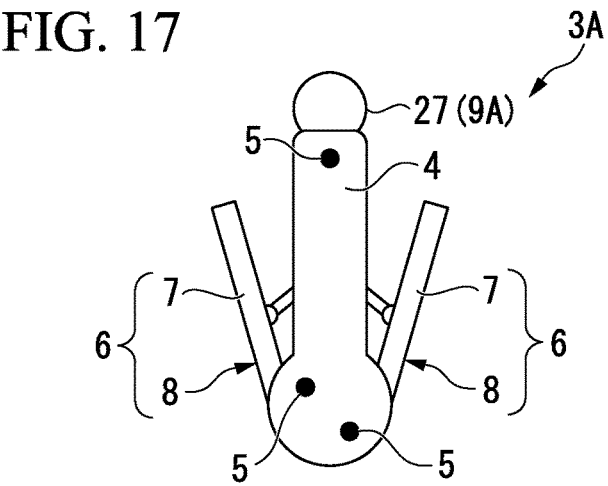
FIG. 17 is a plan view illustrating a object-to-be-detected in another modified example of the second embodiment of the present invention.
Figure 18:
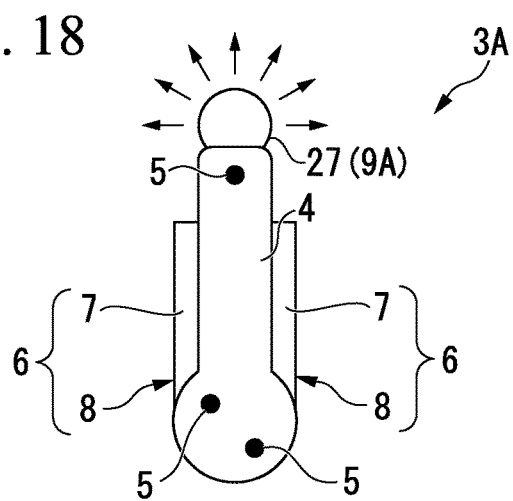
FIG. 18 is a plan view illustrating the object-to-be-detected in the other modified example of the second embodiment of the present invention.

Another modified example 2-2 of the second embodiment will be described below. FIGS. 17 and 18 are plan views illustrating an object-to-be-detected according to the modified example 2-2.

As shown in FIGS. 17 and 18, the modified example 2-2 is different from the above-mentioned modified example, in that a light source 27 of which a light-emitting state varies depending on the opening and closing of the rod-shaped portions 7 of the manipulation part 6 is provided in the second marker 9A instead of the linearly-moving rod 25.

The light source 27 disposed in the second marker 9A varies in at least one of light intensity, blinking period, and color with the opening and closing of the rod-shaped portions 7.

In another example of the method of changing the light intensity of the light source 27, a cover linearly moving similarly to the linearly-moving rod 25 and a light source disposed in the body part 4 and covered with the cover may be provide instead of the linearly-moving rod 25 described in Modified Example 2-1. In this case, the light source may have constant light intensity or constant emission period. In this case, since the cover moves with the manipulation on the manipulation part 6 and the area of the light source covered with the cover varies, the light intensity reaching the detection device 10 also varies.

Third Embodiment

Figure 19:
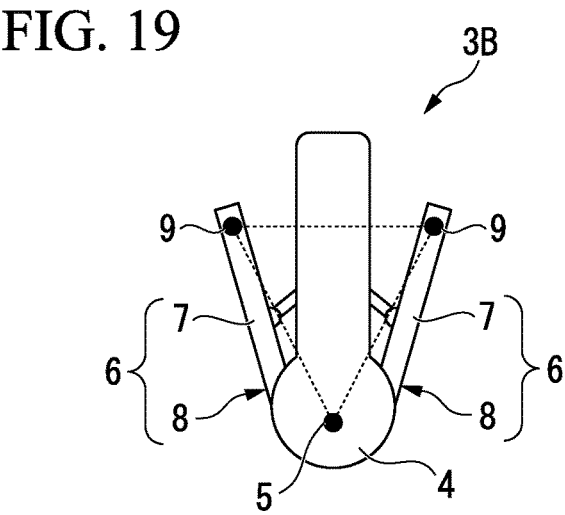
FIG. 19 is a plan view illustrating an object-to-be-detected provided to a operation support device according to a third embodiment of the present invention.
Figure 20:
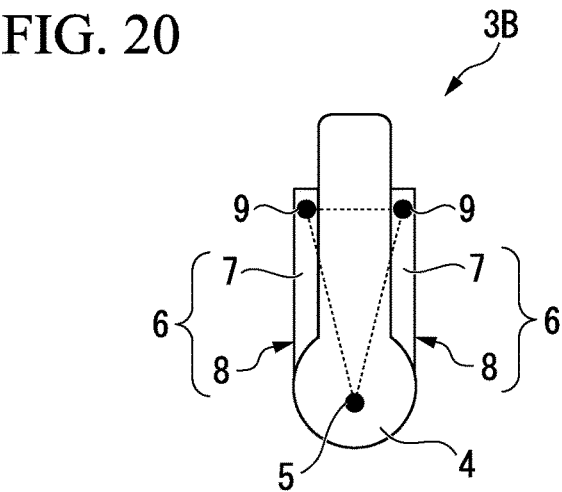
FIG. 20 is a plan view illustrating the object-to-be-detected according to the third embodiment of the present invention.

An operation support device according to a third embodiment of the present invention will be described below. FIGS. 19 and 20 are plan views illustrating an object-to-be-detected disposed in the operation support device according to the third embodiment.

The operation support device 1 is different from the operation support device according to the first embodiment, in that it includes an object-to-be-detected 3B provided instead of the object-to-be-detected 3 described in the first embodiment and a conversion processing unit 22B provided instead of the conversion processing unit 22 described in the first embodiment of the present invention.

The object-to-be-detected 3B includes a body part 4 and a manipulation part 6 as described in the first embodiment and a first marker 5 of which the arrangement is different from that in the first embodiment is disposed in the body part 4.

The first marker 5 is disposed at one position on the outer surface of the body part 4 and second markers 9 are disposed in the respective rod-shaped portions 7 of the manipulation part 6 similarly to the first embodiment.

The distances from the first marker 5 to the second markers 9 are the same and the distance between the second markers 9 is smaller than the distances between the first marker 5 and the second markers 9. Accordingly, even when the manipulation part 6 is opened at any opening degree, three points formed by the first marker 5 and the second markers 9 are vertexes of an equilateral triangle.

The detection device 10 outputs the coordinates of the first marker 5 and the second markers 9 in the working space Q1 to the conversion processing unit 22B.

The conversion processing unit 22B calculates the position of the object-to-be-detected 3 based on the position of the equilateral triangle formed by the first marker 5 and the second markers 9. The conversion processing unit 22B calculates the orientation of the object-to-be-detected 3 based on the direction of the equilateral triangle formed by the first marker 5 and the second markers 9. The distance between the second markers 9 is the length of the bottom side of the equilateral triangle formed by the first marker 5 and the second markers 9 and the bottom side can be recognized to be different from the other sides.

In this way, in the third embodiment, it is possible to detect the position and the orientation of the object-to-be-detected 3 and the manipulation state of the manipulation part 6 by the use of three markers of one marker (the first marker 5) disposed in the body part 4 and the remaining markers (the second markers 9) disposed in the rod-shaped portions 7 of the manipulation part 6, respectively. Accordingly, the number of markers is smaller than that in the object-to-be-detected 3 of the first embodiment. Accordingly, since the space for the markers is reduced, it is possible to easily downsize the object-to-be-detected 3.

Modified Example 3-1

Figure 21:
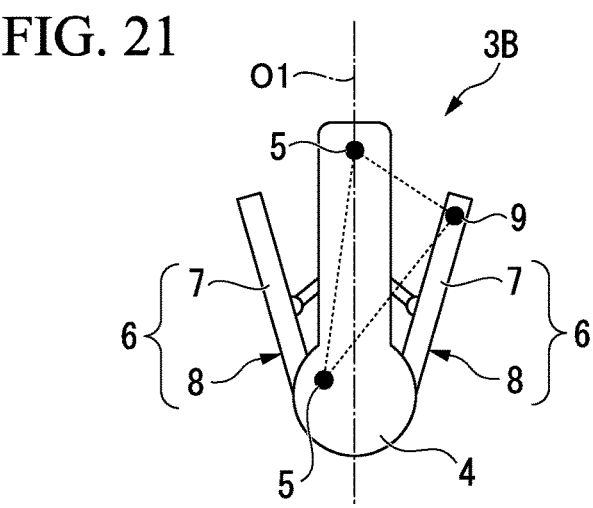
FIG. 21 is a plan view illustrating an object-to-be-detected in a modified example according to the third embodiment of the present invention.
Figure 22:
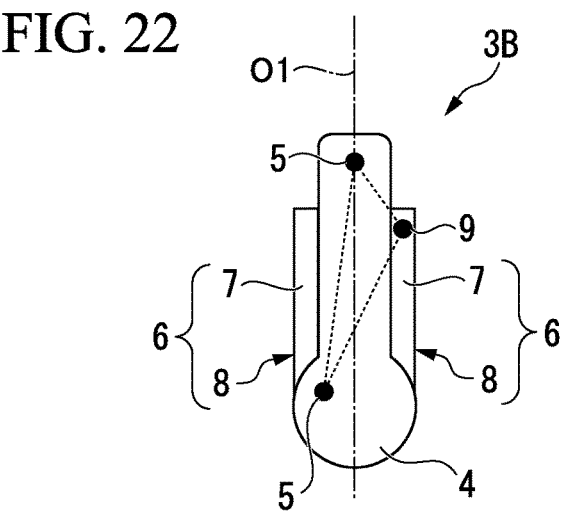
FIG. 22 is a plan view illustrating the object-to-be-detected in the modified example according to the third embodiment of the present invention.

A modified example 3-1 of the above-mentioned embodiment will be described below. FIGS. 21 and 22 are plan views illustrating an object-to-be-detected according to the modified example 3-1.

As shown in FIGS. 21 and 22, the modified example 3-1 is different from the third embodiment, in that two first markers 5 are disposed in the body part 4 and a second marker 9 is disposed in one of the rod-shaped portions 7 in the manipulation part 6.

The two first markers 5 disposed in the body part 4 are located at two positions separated from each other. The distance between the two first markers 5 is constant.

In the modified example 3-1, it is possible to detect the position and the orientation of the object-to-be-detected 3B using three points of the first markers 5 and the second marker 9. It is possible to calculate the central axis O1 of the body part from the position and the orientation of the object-to-be-detected 3B. The distance between the central axis O1 and the second marker 9 can be calculated in the same way as in Modified Example 1-1.

Accordingly, according to the modified example 3-1, it is possible to detect the position and the orientation of the object-to-be-detected 3B and the manipulation input state of the manipulation part 6 using the first markers 5 and the second marker 9.

While the embodiments of the invention have been described in detail with reference to the accompanying drawings, the specific configuration is not limited to the embodiments but the invention includes changes in design without depart from the concept of the invention.

The elements described in the above-mentioned embodiments and the modified examples thereof can be appropriately combined.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An operation support device comprising:
   a manipulation input unit configured to output a manipulation command based on an input from an operator; and
   a motion unit configured to cause a surgical instrument to move based on the manipulation command,
   wherein the manipulation input unit includes
      an object-to-be-detected configured to be gripped by the operator, and
      a detection device that detects the object-to-be-detected,
   wherein the object-to-be-detected includes
      a body part that has a first marker which is detected by the detection device,
      a manipulation part disposed in the body part and configured to be manipulated by the operator, and
      a second marker disposed in at least one of the body part and the manipulation part, wherein a state of the second marker changes in response to a manipulation on the manipulation part,
   wherein the detection device calculates a first information which is capable of specifying a position and an orientation of the object-to-be-detected using at least the first marker and calculates a second information which is capable of specifying a manipulation input state to the manipulation part using at least the second marker, and
   wherein the manipulation input unit outputs a command as the manipulation command to the motion unit based on a result calculated by the detection device, for causing the surgical instrument to move, so as to control a movement of the surgical instrument in accordance with the position of the object-to-be-detected, the orientation of the object-to-be-detected, and the manipulation input state.

2. The operation support device according to claim 1, wherein
   the manipulation part is movably connected to the body part,
   the second marker is disposed in the manipulation part, and
   the detection device calculates a position and an orientation of the body part using at least the first marker and calculates the manipulation input state to the manipulation part based on a position of the second marker.

3. The operation support device according to claim 2, wherein the manipulation part is capable of being opened and closed with respect to the body part.

4. The operation support device according to claim 3, wherein the detection device calculates the position and the orientation of the body part, and the manipulation input state using both the first marker and second marker.

5. The operation support device according to claim 1, wherein
   a first position at which the first marker is located and a second position at which the second marker is located are different from each other,
   the first marker is different from the second marker in at least one item other than the first position and the second position, and
   the detection device distinguishes between the first marker and the second marker based on the item.

6. The operation support device according to claim 5, wherein an amount of state of the second marker changes depending on an amount of manipulation of the manipulation part.

7. The operation support device according to claim 1, wherein
   a first position at which the first marker is located and a second position at which the second marker is located are only different from each other, and
   the detection device distinguishes between the first marker and the second marker based on only a relative positional relationship of the first position of the first marker and the second position of the second marker on the manipulation input unit.

8. An operation support device comprising:
   a master manipulator configured to output a manipulation command based on an input from an operator; and
   a slave manipulator configured to cause a surgical instrument to move based on the manipulation command,
   wherein the master manipulator includes
      an object-to-be-detected configured to be gripped by the operator, and
      a controller that detects the object-to-be-detected,
   wherein the object-to-be-detected includes
      a body part that has a first marker which is detected by the detection device,
      a manipulation part disposed in the body part and configured to be manipulated by the operator, and
      a second marker disposed in at least one of the body part and the manipulation part, wherein a state of the second marker changes in response to a manipulation on the manipulation part,
   wherein the controller is configured to:
      calculate a first information which is capable of specifying a position and an orientation of the object-to-be-detected using at least the first marker;
      calculate a second information which is capable of specifying a manipulation input state to the manipulation part using at least the second marker, and
      output a command as the manipulation command to the slave manipulator based on a result of the calculations of the first and second information, for causing the surgical instrument to move, so as to control a movement of the surgical instrument in accordance with the position of the object-to-be-detected, the orientation of the object-to-be-detected, and the manipulation input state.

9. The operation support device according to claim 8, wherein
the manipulation part is movably connected to the body part,
the second marker is disposed in the manipulation part, and
the controller is further configured to calculate a position and an orientation of the body part using at least the first marker and calculate the manipulation input state to the manipulation part based on a position of the second marker.

10. The operation support device according to claim 9, wherein the manipulation part is capable of being opened and closed with respect to the body part.

11. The operation support device according to claim 10, wherein the controller is further configured to calculate the position and the orientation of the body part, and the manipulation input state using both the first marker and second marker.

12. The operation support device according to claim 8, wherein
a first position at which the first marker is located and a second position at which the second marker is located are different from each other,
the first marker is different from the second marker in at least one item other than the first position and the second position, and
the controller is further configured to distinguish between the first marker and the second marker based on the item.

13. The operation support device according to claim 12, wherein an amount of state of the second marker changes depending on an amount of manipulation of the manipulation part.

14. The operation support device according to claim 8, wherein
a first position at which the first marker is located and a second position at which the second marker is located are only different from each other, and
the controller is further configured to distinguish between the first marker and the second marker based on only a relative positional relationship of the first position of the first marker and the second position of the second marker on the master manipulator.

* * * * *